US012806409B2

(12) United States Patent
Hwang et al.

(10) Patent No.: US 12,806,409 B2
(45) Date of Patent: Nov. 24, 2026

(54) BIO-IMPLANTABLE BLADDER TREATMENT DEVICE, AND METHOD FOR MANUFACTURING ELECTRONIC WEB AND ELECTRONIC THREAD INCLUDED THEREIN

(71) Applicants: KOREA UNIVERSITY RESEARCH AND BUSINESS FOUNDATION, Seoul (KR); SOONCHUNHYANG UNIVERSITY INDUSTRY ACADEMY COOPERATION FOUNDATION, Ansan-si (KR)

(72) Inventors: Suk Won Hwang, Seoul (KR); Eun Kyoung Park, Seoul (KR); Tae Min Jang, Seoul (KR); Joong Hoon Lee, Seoul (KR)

(73) Assignees: Korea University Research and Business Foundation, Seoul (KR); SOONCHUNHYANG UNIVERSITY INDUSTRY ACADEMY COOPERATION FOUNDATION, Asan-si (KR)

( * ) Notice: Subject to any disclaimer, the term of this patent is extended or adjusted under 35 U.S.C. 154(b) by 129 days.

(21) Appl. No.: 18/561,999

(22) PCT Filed: Oct. 27, 2022

(86) PCT No.: PCT/KR2022/016528
§ 371 (c)(1),
(2) Date: Nov. 17, 2023

(87) PCT Pub. No.: WO2023/085653
PCT Pub. Date: May 19, 2023

(65) Prior Publication Data

US 2024/0278003 A1 Aug. 22, 2024

(30) Foreign Application Priority Data

Nov. 11, 2021 (KR) ........................ 10-2021-0154800
Sep. 19, 2022 (KR) ........................ 10-2022-0118167

(51) Int. Cl.
*A61N 1/05* (2006.01)
*A61N 1/36* (2006.01)

(52) U.S. Cl.
CPC ....... *A61N 1/0514* (2013.01); *A61N 1/36007* (2013.01); *A61N 1/36135* (2013.01)

(58) Field of Classification Search
CPC ............ A61N 1/36007; A61N 1/36135; A61B 5/202–205
See application file for complete search history.

(56) References Cited

U.S. PATENT DOCUMENTS 5,277,201 A * 1/1994 Stern ...................... A61B 18/14 606/41
5,836,874 A * 11/1998 Swanson ............ A61B 18/1492 606/41

(Continued)

FOREIGN PATENT DOCUMENTS

CN 101689955 A * 3/2010 ........... H04B 1/0475
CN 107049232 A * 8/2017 ........... A61B 5/4836

(Continued)

OTHER PUBLICATIONS

Mickle, Aaron D., et al. "A wireless closed-loop system for optogenetic peripheral neuromodulation." *Nature* vol. 565 Issue 7739 (Jan. 17, 2019): pp. 361-365.

(Continued)

*Primary Examiner* — Eric D. Bertram
(74) *Attorney, Agent, or Firm* — NSIP Law

(57) ABSTRACT

The present invention relates to a bio-implantable bladder treatment device, and a method for manufacturing an elec- (Continued)

1 tronic web and an electronic thread included therein. The bio-implantable bladder treatment device according to an embodiment of the present invention includes: an electronic web which is installable to cover the outer circumference of the bladder; and an electronic thread inserted into the electronic web to be coupled to the electronic web and configured to measure a state of the bladder.

8 Claims, 15 Drawing Sheets

(56) References Cited

U.S. PATENT DOCUMENTS

| | | | | |
|---|---|---|---|---|
| 9,265,459 | B2 * | 2/2016 | Nagale | A61F 2/0063 |
| 10,085,694 | B2 * | 10/2018 | Nagale | A61B 5/1473 |
| 2013/0090640 | A1 * | 4/2013 | Nagale | A61B 18/1492<br>606/27 |
| 2013/0090648 | A1 * | 4/2013 | Nagale | A61B 5/202<br>606/1 |
| 2015/0164401 | A1 * | 6/2015 | Toth | A61B 5/0538<br>606/41 |
| 2017/0035496 | A1 * | 2/2017 | Nagale | A61N 1/36007 |
| 2018/0116707 | A1 * | 5/2018 | Ben-Ezra | A61B 17/32 |
| 2019/0104933 | A1 * | 4/2019 | Stern | A61B 18/1492 |
| 2021/0069513 | A1 * | 3/2021 | Beer | A61N 1/36007 |

FOREIGN PATENT DOCUMENTS

| | | | | | |
|---|---|---|---|---|---|
| JP | 2016-179228 | | | 10/2016 | |
| JP | 2016179228 | A | * | 10/2016 | A61N 1/37252 |
| JP | 2017-500175 | | | 1/2017 | |
| JP | 2017500175 | A | * | 1/2017 | A61B 18/1492 |
| JP | 2019-177187 | | | 10/2019 | |
| JP | 2019177187 | A | * | 10/2019 | A61M 27/002 |
| JP | 2021-506436 | | | 2/2021 | |
| JP | 2021506436 | A | * | 2/2021 | A61B 5/6837 |
| JP | 2022-506203 | | | 1/2022 | |
| JP | 2022506203 | A | * | 1/2022 | A61B 5/20 |
| KR | 10-2003-0035794 | A | | 5/2003 | |
| KR | 10-2009-0020548 | A | | 2/2009 | |
| KR | 10-2011-0051046 | A | | 5/2011 | |
| KR | 10-2011-0088004 | A | | 8/2011 | |
| KR | 101689955 | B1 | * | 12/2016 | A61N 5/0601 |
| KR | 10-2018-0088056 | A | | 8/2018 | |

OTHER PUBLICATIONS

Jang, Tae-Min, et al. “Expandable and implantable bioelectronic complex for analyzing and regulating real-time activity of the urinary bladder.” *Science advances* vol. 6 Issue 46 (Nov. 11, 2020): eabc9675. pp. 1-13.

* cited by examiner

BIO-IMPLANTABLE BLADDER TREATMENT DEVICE, AND METHOD FOR MANUFACTURING ELECTRONIC WEB AND ELECTRONIC THREAD INCLUDED THEREIN

CROSS REFERENCE TO RELATED APPLICATIONS

This application is a U.S. National Stage Application of International Application No. PCT/KR2022/016528, filed on Oct. 27, 2022, which claims the benefit under 35 USC 119(a) and 365(b) of Korean Patent Application Nos. 10-2021-0154800, filed on Nov. 11, 2021 and 10-2022-0118167, filed on Sep. 19, 2022, in the Korean Intellectual Property Office, the entire disclosures of which are incorporated herein by reference for all purposes.

TECHNICAL FIELD

The present invention relates to a bio-implantable bladder treatment device and a method for manufacturing an electronic web and an electronic thread included in the same, and more particularly, to a bio-implantable bladder treatment device and a method for manufacturing an electronic web and an electronic thread included in the same installed on an outside of a bladder to cover the outside of the bladder without an adhesive or a surgical procedure so as to monitor the bladder and apply stimulus for treatment.

BACKGROUND ART

Most urinary diseases are chronic diseases and require continuous diagnosis and treatment. However, there is no device that can be used consistently in daily life to treat the urinary diseases.

Preclinical bladder monitoring diagnoses a state (pressure) of the bladder through a catheter surgically inserted into an upper portion of the bladder. However, the above approach is negative for a disease treatment research because errors in measurement values are caused by stimulating the bladder and direct information on a bladder volume serving as an important variable in bladder changes cannot be obtained and may be accurate.

In clinical practice, the urodynamic test is used to figure out the physiological characteristics of the bladder. the condition (pressure) of the bladder is measured through a process of inserting a tube for measuring a pressure into the bladder and anus and then filling and emptying the bladder with a saline solution. The above test approach causes considerable discomfort and pain to the patient, and especially continuous measurement is impossible for the patient in a daily life, so it is difficult to make a comprehensive diagnosis on a status of the bladder disease.

Ultrasound equipment for diagnosing a state of the bladder in vitro has been developed but has limitations in clinical use of treating the urinary disease due to inaccurate diagnosis and lack of therapeutic function.

DISCLOSURE

Technical Problem

The present invention provides a bio-implantable bladder treatment device and a method for manufacturing an electronic web and an electronic thread included in the same so as to be installed on an outside of a bladder without an adhesive or a surgical procedure.

In addition, the present invention provides a bio-implantable bladder treatment device and a method for manufacturing an electronic web and an electronic thread included in the same so as to effectively monitor a state of a bladder.

In addition, the present invention provides a bio-implantable bladder treatment device and a method for manufacturing an electronic web and an electronic thread included in the same so as to effectively apply stimulus for treating a bladder in response to a state of the bladder.

Technical Solution

An aspect of the present invention provides a bio-implantable bladder treatment device including: an electronic web installable to cover an outer circumference of a bladder; and an electronic thread inserted into the electronic web so as to be coupled to the electronic web and configured to measure a state of the bladder.

In addition, the electronic web may include: an inner support portion provided in a ring shape; an outer support portion provided in a ring shape, and positioned in an area outside the inner support portion; and an auxiliary support portion for connecting the inner support portion and the outer support portion to each other.

In addition, the inner support portion and the outer support portion may include a winding part in at least one section.

In addition, the auxiliary support portion may include a winding part in at least one section.

In addition, the electronic web further includes: a buckle portion connected to the auxiliary support portion, and formed therein with a hole into which the electronic thread is inserted.

In addition, the electronic web further includes: a therapeutic stimulus generation member positioned on one side of the electronic web to generate electrical stimulus.

In addition, the therapeutic stimulus generation member may include a first electrode and a second electrode paired with each other.

In addition, the electronic thread may include: a sensor support plate provided as a thread structure having a preset width; and a sensor module attached to a top surface of the sensor support plate, and including a sensor for detecting a state of the bladder.

In addition, the sensor may include at least one of a strain sensor, a temperature sensor and an electromyography sensor.

In addition, the electronic thread further includes: a therapeutic stimulus generation member attached to a bottom surface of the sensor support plate to generate stimulus for treating the bladder.

Another aspect of the present invention provides a method for manufacturing an electronic web for a bio-implantable bladder treatment device, which includes: forming a separation auxiliary film in an electronic web forming mold; filling the electronic web forming mold with an electronic web forming material; and separating an electronic web from the electronic web forming mold when the electronic web forming material is cured, wherein the electronic web forming material is provided as an elastic polymer material.

Still another aspect of the present invention provides a method for manufacturing an electronic thread for a bio-implantable bladder treatment device, which includes: forming a soluble separator on a sensor module forming substrate; forming a sensor module by sequentially forming a sensor protective layer and a sensor layer on a top surface of the soluble separator; immersing the sensor module forming substrate in a separator removal solvent to dissolve the soluble separator, thereby separating the sensor module; and transferring the sensor module to a top surface of a sensor support plate.

Advantageous Effects

One embodiment of the present invention provides a bio-implantable bladder treatment device and a method for manufacturing an electronic web and an electronic thread included in the same, so that the bio-implantable bladder treatment device can be installed on an outside of a bladder without an adhesive or a surgical procedure.

In addition, one embodiment of the present invention provides a bio-implantable bladder treatment device and a method for manufacturing an electronic web and an electronic thread included in the same, so that a state of a bladder can be effectively monitored.

In addition, one embodiment of the present invention provides a bio-implantable bladder treatment device and a method for manufacturing an electronic web and an electronic thread included in the same, so that stimulus for treating a bladder can be effectively applied in response to a state of the bladder.

BEST MODE

Mode for Invention

Hereinafter, exemplary embodiments of the present invention will be described in detail with reference to the accompanying drawings. However, the technical idea of the present invention is not limited to the exemplary embodiments described herein and may be embodied in other forms. Further, the embodiments are provided to enable contents disclosed herein to be thorough and complete and provided to enable those skilled in the art to fully understand the idea of the present invention.

Herein, when one component is mentioned as being on another component, it signifies that the one component may be placed directly on the other component or a third component may be interposed therebetween. In addition, in drawings, thicknesses of layers and areas may be exaggerated to effectively describe the technology of the present invention.

In addition, although terms such as first, second and third are used to describe various components in various embodiments of the present specification, the components will not be limited by the terms. The above terms are used merely to distinguish one component from another. Accordingly, a first component referred to in one embodiment may be referred to as a second component in another embodiment. Each embodiment described and illustrated herein may also include a complementary embodiment. In addition, the term "and/or" is used herein to include at least one of the components listed before and after the term.

The singular expression herein includes a plural expression unless the context clearly specifies otherwise. In addition, it will be understood that the term such as "include" or "have" herein is intended to designate the presence of feature, number, step, component, or a combination thereof recited in the specification, and does not preclude the possibility of the presence or addition of one or more other features, numbers, steps, components, or combinations thereof. In addition, the term "connection" is used herein to include both indirectly connecting a plurality of components and directly connecting the components.

In addition, in the following description of the embodiments of the present invention, the detailed description of known functions and configurations incorporated herein will be omitted when it possibly makes the subject matter of the present invention unclear unnecessarily.

Figure 1:
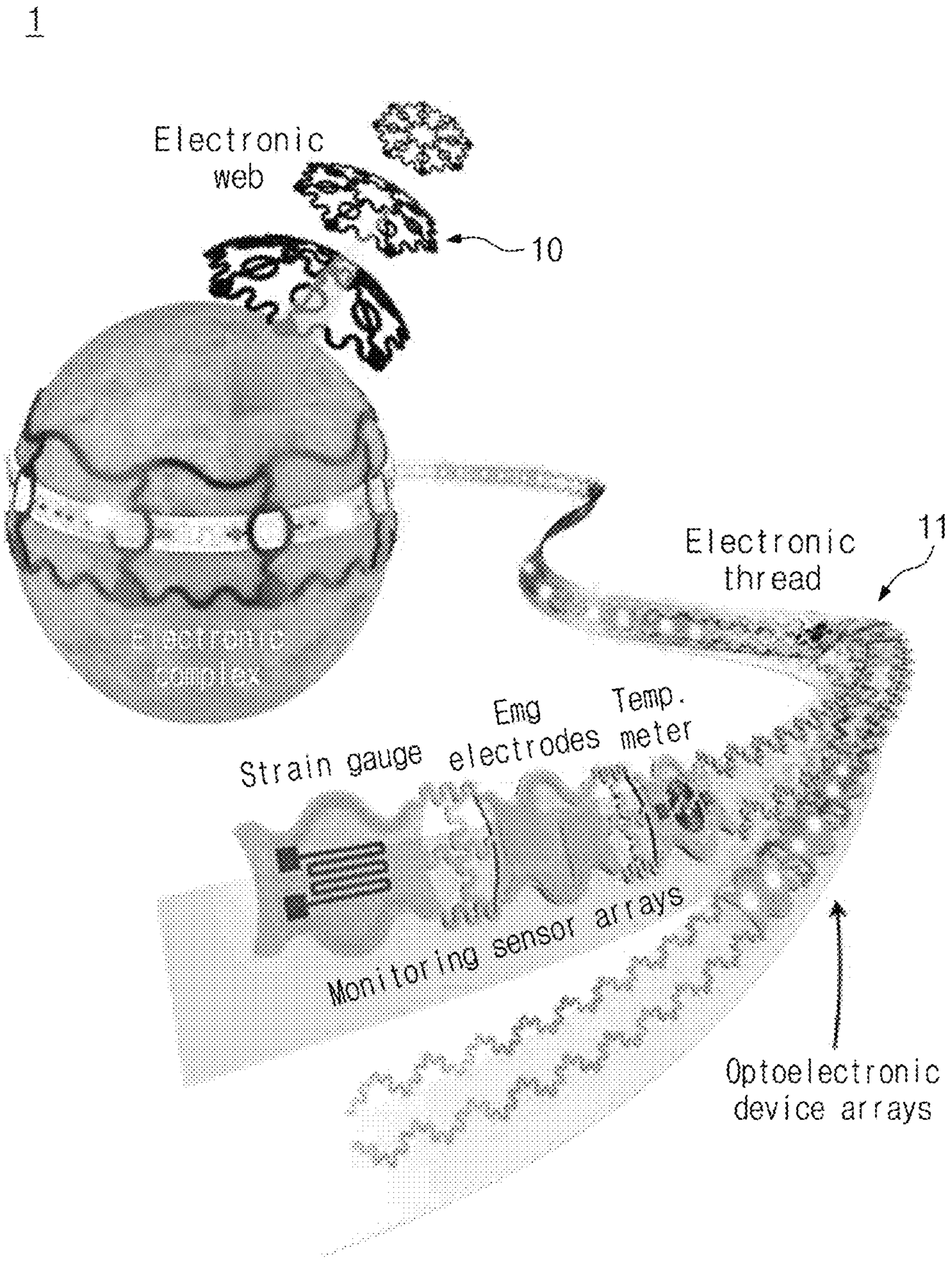
FIG. 1 is a view showing a bio-implantable bladder treatment device according to a first embodiment of the present invention.

FIG. 1 is a view showing a bio-implantable bladder treatment device according to a first embodiment of the present invention.

Figure 8:
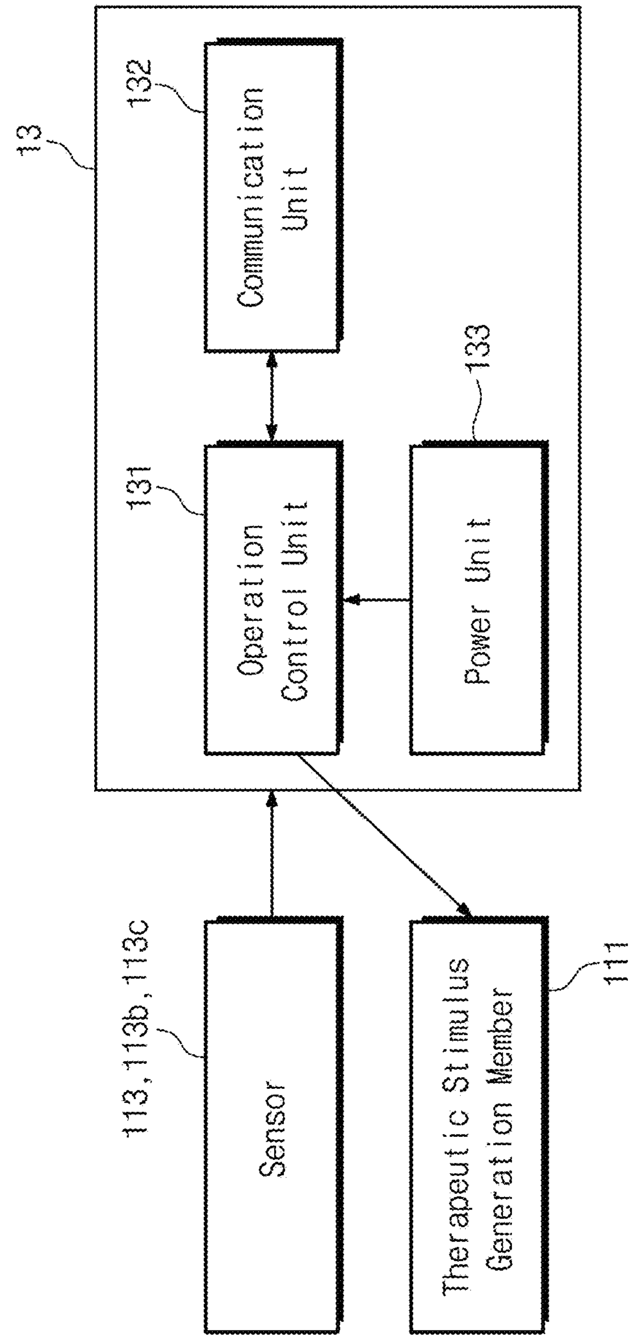
FIG. 8 is a view showing a control relationship of the bio-implantable bladder treatment device according to the first embodiment of the present invention.

Referring to FIG. 1, A bio-implantable bladder treatment device 1 according to the first embodiment of the present invention includes an electronic web 10, an electronic thread 11 and a controller 13 (in FIG. 8).

The bio-implantable bladder treatment device 1 according to the first embodiment of the present invention is provided to be installed to an outer circumference of a bladder so as to monitor an activity of the bladder and apply therapeutic stimulus for healing urinary disorders and stimulating a urinary activity to the bladder.

The electronic web 10 is provided to be installable to cover the outer circumference of the bladder. The electronic web 10 is formed of an elastic material. The electronic web 10 is formed of a polymer material. The electronic web 10 may be formed of a rubber material to have elasticity. For example, the electronic web 10 may be formed of a silicone-based rubber material, biodegradable plastic, biopolymer, poly-butylene adipate terephthalate (PBAT) or the like.

Figure 2:
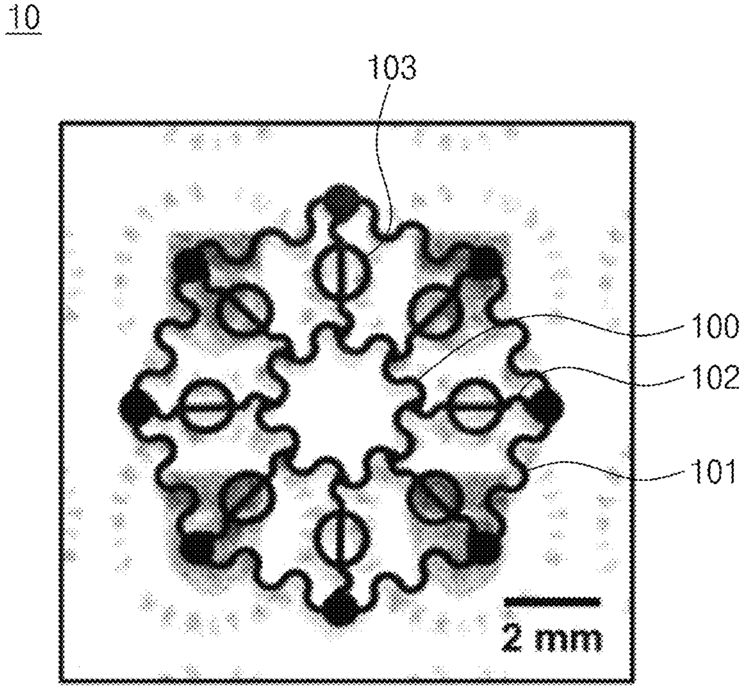
FIG. 2 is a view showing an electronic web of FIG. 1.

FIG. 2 is a view showing an electronic web of FIG. 1.

Referring to FIG. 2, the electronic web 10 includes an inner support portion 100, an outer support portion 101, an auxiliary support portion 102 and a buckle portion 103.

The inner support portion 100 is provided in a ring shape. The inner support portion may be provided to include a winding part in at least one section. Accordingly, the inner support portion 100 may have a shape transformed so that the winding part is straightened.

The outer support portion 101 may be provided in a ring shape, and positioned in an area outside the inner support portion 100. The outer support portion 101 may be provided to include a winding part in at least one section. Accordingly, the outer support portion 101 may have a shape transformed so that the winding part is straightened.

The auxiliary support portion 102 is provided to connect the inner support portion 100 and the outer support portion 101 to each other. At least one auxiliary support portion 102 may be provided in a circumferential direction of the inner support portion 100 and the outer support portion 101. When a plurality of auxiliary support portions 102 are provided, the auxiliary support portions 102 may be arranged at equal intervals from each other in the circumferential direction of the inner support portion 100 and the outer support portion 101. In addition, the auxiliary support portions 102 may be arranged to face each other about the inner support portion 100. the auxiliary support portion 102 may be provided to include a winding part in at least one section. Accordingly, the auxiliary support portion 102 may have a shape transformed so that the winding part is straightened.

The buckle portion 103 is provided to be connected to the auxiliary support portion 102. The buckle portion 103 may be provided to form at least one hole, so that a linear structure is inserted and connected thereto. For example, the buckle portion 103 may be formed in a ring shape and connected to a partial section of the auxiliary support portion 102, so that one hole is formed in each of both sides of the auxiliary support portion 102. The buckle portion 103 may be provided on all of the auxiliary support portions 102 or formed on some of the auxiliary support portions 102.

Figure 3:
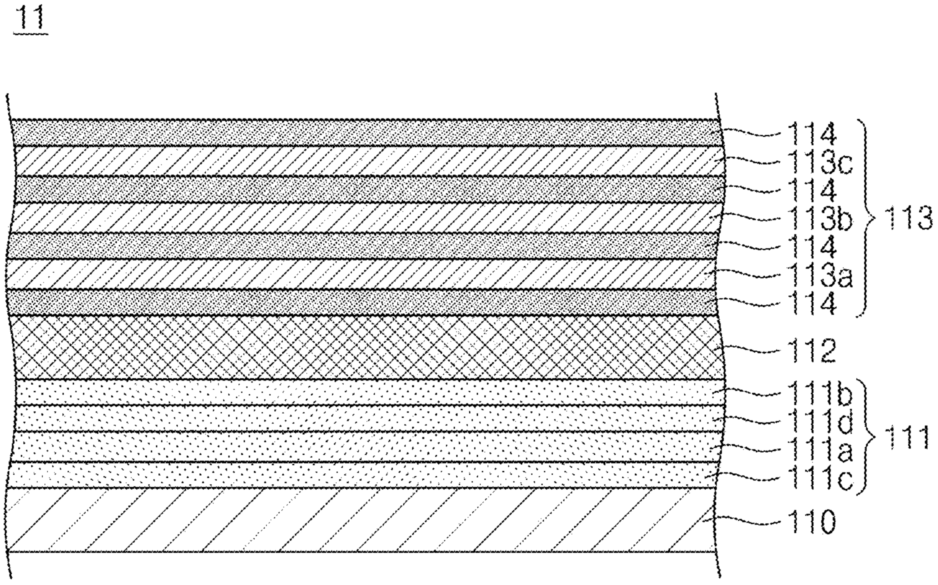
FIG. 3 is a view schematically showing a longitudinal sectional structure of an electronic thread in FIG. 1.
Figure 4:
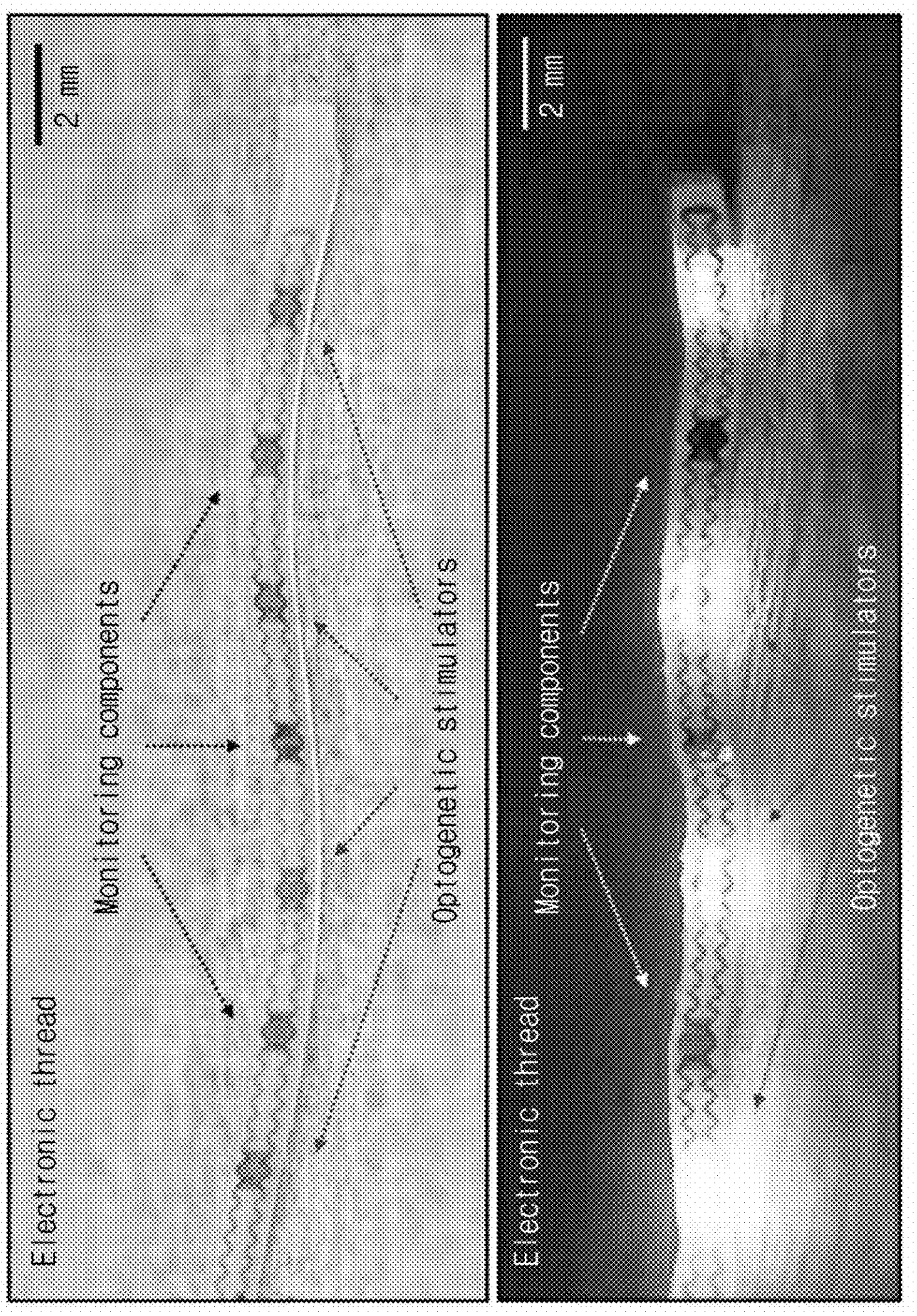
FIG. 4 is a view showing an electronic thread made according to an experimental example.

FIG. 3 is a view schematically showing a longitudinal sectional structure of an electronic thread in FIG. 1. FIG. 4 is a view showing an electronic thread made according to an experimental example.

Referring to FIGS. 3 and 4, the electronic thread 11 includes a support plate 110, a therapeutic stimulus generation member 111, a sensor support plate 112, and a sensor module 113.

The electronic thread 11 measures a state of the bladder.

The support plate 110 is provided as a thread structure having a preset width. The width of the support plate 110 is provided to correspond to a size of the hole of the buckle portion 103 so as to be inserted into the buckle portion 103. The support plate 110 is formed of a polymer material. The support plate 110 is formed of an elastic material. For example, the support plate 110 may be formed of a silicone-based rubber material, biodegradable plastic, biopolymer, poly-butylene adipate terephthalate (PBAT) or the like. The support plate 110 may have a thickness of tens of micrometers. The support plate 110 may be provided opaquely. For example, the support plate 110 may be formed of a polymer material mixed with a dye material, such as a white dye material, so as to be colored. Accordingly, the support plate 110 has lowered light transmittivity and improved light reflectivity.

The therapeutic stimulus generation member is provided to be attached to a top surface of the support plate 110. The therapeutic stimulus generation member includes stimulus generation layers 111*a* and 111*b* and stimulus generation protective layers 111*c* and 111*d*.

The stimulus generation layers 111*a* and 111*b* generate stimulus for treating the bladder. The stimulus generation layers 111*a* and 111*b* may be provided to emit light to serve as an optogenetic stimulator for optogenetically treating the bladder through the emitting light. The stimulus generation layers 111*a* and 111*b* include LEDs 111*b* arranged in a longitudinal direction of the electronic thread 11, and an LED lead wire 111*a* for connecting the LEDs 111*b* to each other. The LEDs 111*b* may be attached to an upper part of the LED lead wire 111*a*.

The stimulus generation protective layers 111*c* and 111*d* are coated on the stimulus generation layers 111*a* and 111*b* to protect the stimulus generation layers 111*a* and 111*b*. The stimulus generation protective layers 111*c* and 111*d* may be an organic polymer compound. The stimulus generation protective layers 111*c* and 111*d* may be plastic such as polyimide. The stimulus generation protective layers 111*c* and 111*d* includes first stimulus generation protective layer 111*c* and second stimulus generation protective layer 111*d*. The first stimulus generation protective layer 111*c* is coated on a lower surface of the stimulus generation layers 111*a* and 111*b* so as to be attached to the support plate 110. In addition, the second stimulus generation protective layer 111*d* is coated on a top surface of the LED lead wire 111*a* so as to be positioned between the LEDs 111*b* and the LED lead wire 111*a*.

The sensor support plate 112 is attached to a top surface of the therapeutic stimulus generation member 111. The sensor support plate 112 is provided as a thread structure having a width corresponding to the support plate 110. The sensor support plate 112 is formed of a polymer material. The sensor support plate 112 is formed of an elastic material. For example, the sensor support plate 112 may be formed of a silicone-based rubber material, biodegradable plastic, biopolymer, poly-butylene adipate terephthalate (PBAT) or the like. The sensor support plate 112 may have a thickness of tens of micrometers. The sensor support plate 112 may be provided transparently. Accordingly, the sensor support plate 112 is provided to have high light transmittivity.

The sensor module 113 detects a state of the bladder. The sensor module 113 is attached to a top surface of the sensor support plate 112. The sensor module 113 includes a sensor layer 113*a*, 113*b* and 113*c* and a sensor protective layer 114.

The sensor layer 113*a*, 113*b* and 113*c* is provided to include a sensor (that is, a monitoring element) that detects a state of the bladder. The sensor layer 113*a*, 113*b* and 113*c* includes a strain sensor layer 113*a*, a temperature sensor layer 113*b*, and an electromyography sensor layer 113*c*. The sensor includes a strain sensor, a temperature sensor, an electromyography sensor.

The strain sensor layer 113*a* is provided to detect strain. The strain sensor layer 113*a* includes a strain sensor and a strain sensor lead wire for connecting the strain sensor. A plurality of strain sensors may be provided to be spaced apart along the strain sensor lead wire.

The temperature sensor layer 113*b* is provided to detect a temperature. The temperature sensor layer 113*b* includes a temperature sensor and a temperature sensor lead wire for connecting the temperature sensor. A plurality of temperature sensors may be provided to be spaced apart along the temperature sensor lead wire.

The electromyography sensor layer 113*c* is provided to detect electromyography. The electromyography sensor layer 113*c* includes an electromyography sensor and an electromyography sensor lead wire for connecting the electromyography sensor. A plurality of electromyography sensors may be provided to be spaced apart along the electromyography sensor lead wire.

The strain sensor layer 113*a*, the temperature sensor layer 113*b*, and the electromyography sensor layer 113*c* are laminated with each other. The strain sensor layer 113*a*, the temperature sensor layer 113*b*, and the electromyography sensor layer 113*c* have no limit for the laminated sequence. In other words, one of the strain sensor layer 113*a*, the temperature sensor layer 113*b*, and the electromyography sensor layer 113*c* may be position at the bottom, one of the remaining two layers may be positioned thereon, and the remaining one layer may be positioned on the top.

The sensor protective layer 114 may be positioned between the strain sensor layer 113*a*, the temperature sensor layer 113*b*, and the electromyography sensor layer 113*c*. In addition, the sensor protective layer 114 may be positioned on top and bottom surfaces of the sensor layers 113*a*, 113*b*, and 113*c* in which the strain sensor layer 113*a*, the temperature sensor layer 113*b*, and the electromyography sensor layer 113*c* are laminated.

Figure 5:
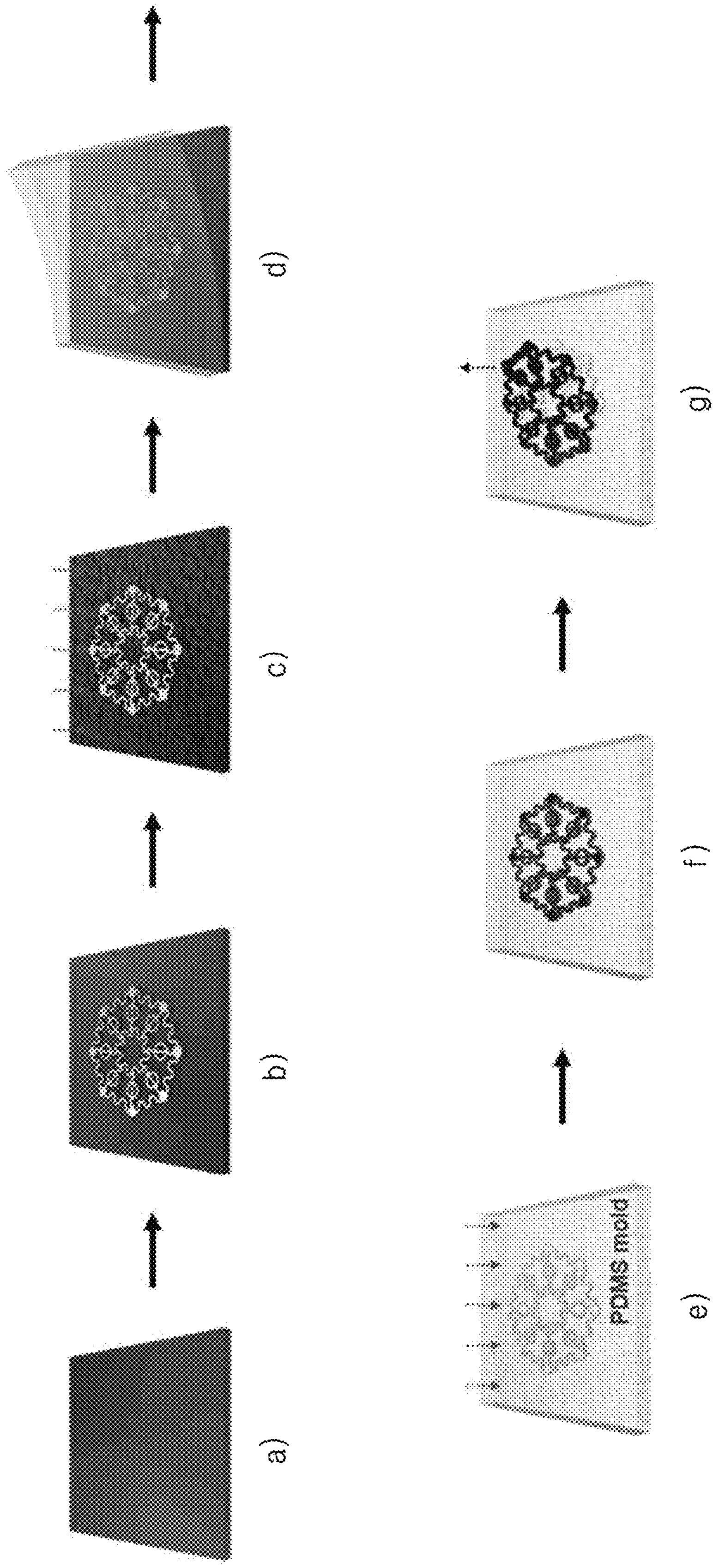
FIG. 5 is a view showing a manufacturing process of an electronic web.

FIG. 5 is a view showing a manufacturing process of an electronic web.

Hereinafter, a method for manufacturing the electronic web will be described with reference to FIG. 5.

a) A mold forming substrate is prepared. The mold forming substrate may be use as a silicon substrate or the like.

b) A pattern is formed on the mold forming substrate. The pattern may be formed through a photolithography process by using photoresist. In the present experimental example, the pattern is formed to have a thickness of 50 μm to 300 μm through a photolithography process by using SU-8 photoresist on a mold forming substrate which is a silicon substrate.

c) An anti-adhesion film is formed on the mold forming substrate on which the pattern is formed. The anti-adhesion film may be formed by depositing and annealing an anti-adhesion film forming material, and Accordingly, the anti-adhesion film may be formed as a self-assembled monolayer (SAM). The anti-adhesion film forming material may include alkyltrichlorosilane, alkyltrimethoxysilane, alkyltriethoxysilane, polytetrafluoroethylene (PTFE), perfluoroalkoxy alkane (PFA), dichlorodimethylsilane (DDMS), perfluorodecyltrichlorosilane (FDTS), fluorooctyltrichlorosilane (FOTS), octadecyltrimethoxysilane (OTMS) and the like. In the present experimental example, fluorooctyltrichlorosilane (FOTS) is deposited and annealed to form an anti-adhesion film in the form of a self-assembled monolayer.

d) An electronic web forming mold is manufactured by applying the mold forming material to the mold forming substrate, curing the applied mold forming material, and then separating the cured the mold forming material from the mold forming substrate. The electronic web forming mold may be effectively separated from the mold forming substrate through the anti-adhesion film. The mold forming material may be a silicone-based and urethane-based rubber material. In the present experimental example, an electronic web forming mold formed of poly(dimethylsiloxane) (PDMS) is manufactured by mixing Sylgard A and B in the ratio of 10:1 and applying and curing the mixed Sylgard A and B on the mold forming substrate.

e) An auxiliary separation film is formed in the electronic web forming mold. The auxiliary separation film is formed by depositing and annealing an auxiliary separation film forming material, and accordingly, the auxiliary separation film may be self-assembled monolayer (SAM). The auxiliary formed as a separation film forming material may include alkyltrichlorosilane, alkyltrimethoxysilane, polytetrafluoroethylene (PTFE), alkyltriethoxysilane, perfluoroalkoxy alkane (PFA), dichlorodimethylsilane (DDMS), perfluorodecyltrichlorosilane (FDTS), fluorooctyltrichlorosilane (FOTS), octadecyltrimethoxysilane (OTMS) and the like. In the present experimental example, fluorooctyltrichlorosilane (FOTS) is deposited and annealed to form an auxiliary separation film in the form of a self-assembled monolayer.

f) The electronic web forming mold is filled with the electronic web forming material. In the present experimental example, ecoflex is used as the electronic web forming material.

g) When the electronic web forming material is cure, the cured electronic web forming material is separated from the electronic web forming mold, so that the manufacturing of the electronic web 10 is completed. Due to the auxiliary separation film, the cured electronic web 10 may be effectively separated from the electronic web forming mold.

Figure 6:
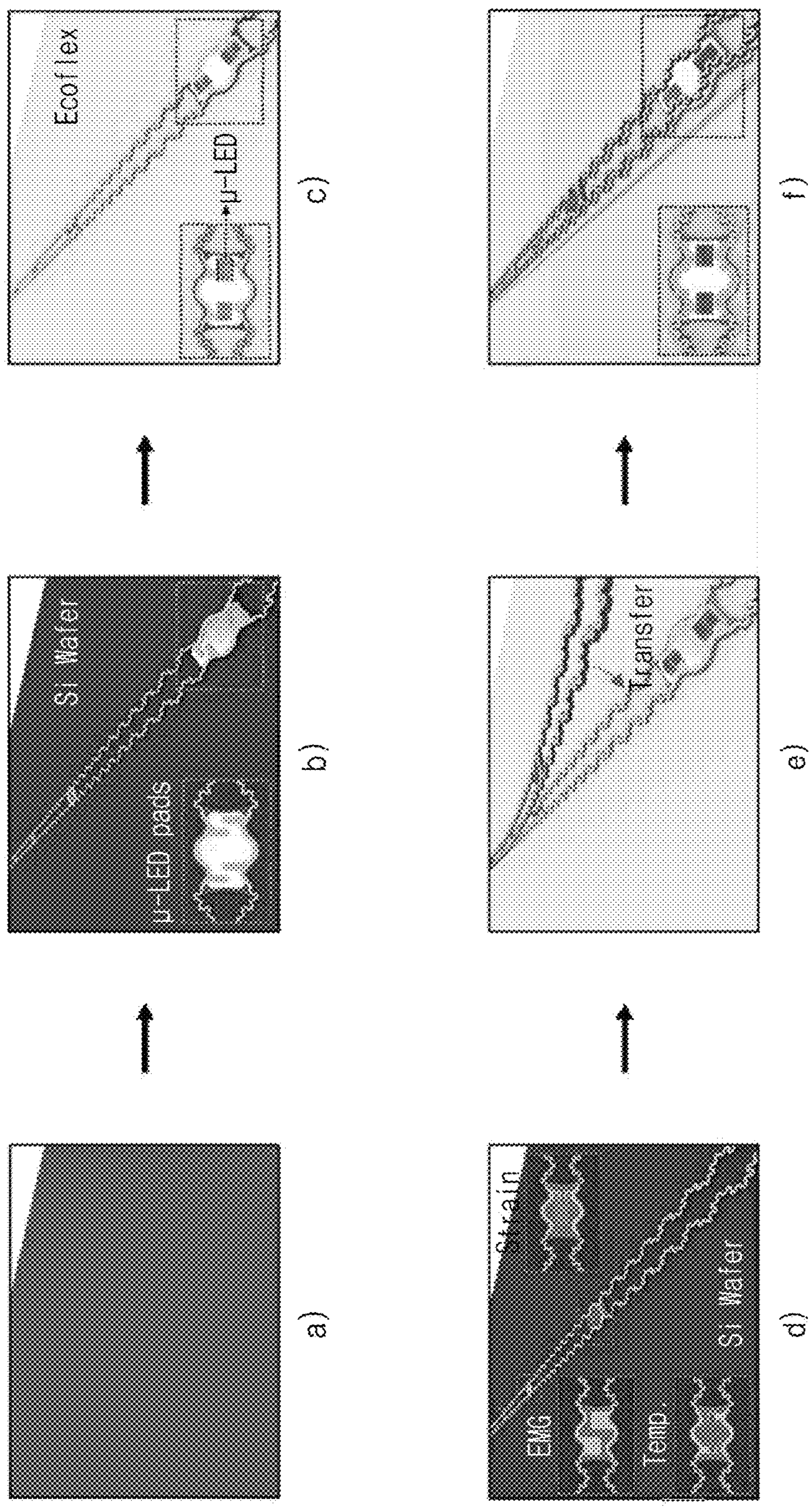
FIG. 6 is a view showing a manufacturing process of an electronic thread.

FIG. 6 is a view showing a manufacturing process of an electronic thread.

Hereinafter, a method for manufacturing the electronic thread 11 will be described with reference to FIG. 6.

a) A soluble separator is formed as a film shape on a therapeutic stimulus generation member forming substrate, and a first stimulus generation protective layer 111*c* is formed as a film shape on a top surface of the soluble separator. In the present experimental example, a silicon substrate or the like is used as the therapeutic stimulus generation member forming substrate. In addition, the soluble separator is formed as a film having a thickness of 50 nm to 500 nm using poly(methyl methacrylate) (PMMA). In addition, the first stimulus generation protective layer 111*c* is formed as a film having a thickness of 1 μm to 10 μm using polyimide (PI).

b) An LED lead wire 111*a* and a second stimulus generation protective layer 111*d* are sequentially formed on a top surface of the first stimulus generation protective layer 111*c*.

The LED lead wire 111*a* is formed through deposition after an LED lead wire forming pattern is formed on the top surface of the previously formed first stimulus generation protective layer 111*c*. The LED lead wire forming pattern is formed through a photolithography process. The LED lead wire 111*a* may be deposited through a thermal evaporator, a sputtering, an electron beam evaporator or the like. In the present experimental example, the LED lead wire 111*a* is deposited through an electron beam evaporator. The LED lead wire 111*a* may be deposited separately as a lower adhesive layer and a main lead wire layer. The lower adhesive layer is formed by depositing chromium (Cr), titanium (Ti) and the like to have a thickness of 3 nm to 10 nm, and the main lead wire layer is formed by depositing gold (Au), copper (Cu) and the like to have a thickness of 500 nm or more on an upper side of the lower adhesive layer. The main lead wire layer functions to connect the LEDs 111*b* to each other. When a thickness thereof is less than 500 nm, the deviation in emission intensity of the LEDs 111*b* significantly increases due to a decrease in conductivity, and accordingly performance deterioration may occur.

The second stimulus generation protective layer 111*d* is formed as a film having a thickness of 1 μm to 10 μm using polyimide (PI). Thereafter, the second stimulus generation protective layer 111*d* is etched to expose a point for connecting the LED 111*b* and the LED lead wire 111*a*. Specifically, the second stimulus generation protective layer 111*d* is etched after a pattern for etching the stimulus generation protective layer is formed through a photolithography process. In the present experimental example, the second stimulus generation protective layer 111*d* is etched by using a reactive ion etcher.

c) The therapeutic stimulus generation member forming substrate is immersed in a separator removal solvent to dissolve the soluble separator, so that the therapeutic stimulus generation member 111, which is being manufactured, is separated from the therapeutic stimulus generation member forming member. In the present experimental example, acetone, which can dissolve poly(methyl methacrylate), is used as the separator removal solvent. Thereafter, the therapeutic stimulus generation member 111 being manufactured is transferred to a prepared support plate 110 so that the first stimulus generation protective layer 111*c* faces the support plate 110. The support plate 110 may be provided in a state formed through a scheme, such as spin coating or drop casting, on an electronic thread forming substrate. In the present experimental example, the support plate 110 is formed to have a thickness of 30 μm to 60 μm using ecoplex mixed with a white dyeing material on the electronic thread forming substrate an as a glass substrate, and then the therapeutic stimulus generation member 111 being manufactured is transferred to the support plate 110 by using a polydimethylsiloxane (PDMS) stamp, a high temperature peeling tape, a water peeling tape or the like. Thereafter, the LED (111*b*) is positioned on a top surface of the second stimulus generation protective layer 111*d*, and the LED 111*b* is connected to the LED lead wire 111*a* by using a solder material such as silver epoxy. The LED 111*b* has a thickness ranged from 5 μm to 50 μm. The LED 111*b* and the LED lead wire 111*a* may be heat hardened to be tightly connected electrically and physically. Thereafter, a second support plate 110 is formed on the top surface of the therapeutic stimulus generation member 111. In the present experimental example, the second support plate 110 is formed by coating to have a thickness of 30 μm to 60 μm using ecoplex.

d) A soluble separator is formed as a film shape on a sensor module forming substrate, and a sensor protective layer 114 and a sensor layer 113*a*, 113*b* and 113*c* are sequentially formed on a top surface of the soluble separator. The sensor protective layer 114 is formed on the uppermost surface of the sensor module 113.

In the present experimental example, a silicon substrate is used as the sensor module forming substrate. In addition, the soluble separator is formed as a film having a thickness of 50 nm to 500 nm using poly(methyl methacrylate) (PMMA). In addition, the sensor protective layer 114 is formed as a film having a thickness of 1 μm to 10 μm using polyimide (PI).

In addition, in the strain sensor layer 113*a*, a strain sensor is formed by depositing a material, such as silicon (Si), gold (Au) and platinum (Pt), on a separate substrate through a scheme such as an electron beam evaporator, a thermal evaporator and sputtering, and then formed to have a thickness of 50 nm to 500 nm on a top surface of the sensor protective layer 114 previously formed through transfer from another substrate. Thereafter, the strain sensor lead wire is formed through deposition after a lead wire forming pattern for the strain sensor is formed. The lead wire forming pattern for the strain sensor is formed through a photolithography process. The strain sensor lead wire may be deposited separately as a lower adhesive layer and a main lead wire layer. The lower adhesive layer is formed by depositing chromium (Cr), titanium (Ti) and the like to have a thickness of 3 nm to 10 nm, and the main lead wire layer is formed by depositing gold (Au), copper (Cu) or the like to have a thickness of 500 nm or more on an upper side of the lower adhesive layer. Thereafter, the sensor protective layer 114 is formed on a top surface thereof. The sensor protective layer 114 is formed as a film having a thickness of 1 μm to 10 μm using polyimide (PI).

In addition, in the temperature sensor layer 113*b*, the temperature sensor is formed on the previously formed sensor protective layer 114 after being deposited and patterned to have a thickness of 30 nm to 100 nm using a material such as gold (Au) and platinum (Pt). Thereafter, a temperature sensor lead wire is formed. The temperature sensor lead wire is formed through deposition after a lead wire forming pattern for the temperature sensor is formed. The lead wire forming pattern for the temperature sensor is formed through a photolithography process. The temperature sensor lead wire may be deposited separately as a lower adhesive layer and a main lead wire layer. The lower adhesive layer is formed by depositing chromium (Cr), titanium (Ti) and the like to have a thickness of 3 nm to 10 nm, and the main lead wire layer is formed by depositing gold (Au), copper (Cu) and the like to have a thickness of 500 nm or more on an upper side of the lower adhesive layer. Thereafter, the sensor protective layer 114 is formed on a top surface thereof.

In addition, in the electromyography sensor layer 113*c*, an electromyography sensor is formed on the previously formed sensor protective layer 114 after being deposited and patterned to have a thickness of 100 nm to 1000 nm using a material such as gold (Au) and platinum (Pt). Thereafter, an electromyography sensor lead wire is formed. The electromyography sensor lead wire is formed through deposition after a lead wire forming pattern for the electromyography sensor is formed. The lead wire forming pattern for the electromyography is formed through a photolithography process. The electromyography sensor lead wire may be deposited separately as a lower adhesive layer and a main lead wire layer. The lower adhesive layer is formed by depositing chromium (Cr), titanium (Ti) and the like to have a thickness of 3 nm to 10 nm, and the main lead wire layer is formed by depositing gold (Au), copper (Cu) and the like to have a thickness of 500 nm or more on an upper side of the lower adhesive layer. Thereafter, the sensor protective layer 114 is formed on a top surface thereof.

e) The sensor module forming substrate is immersed in a separator removal solvent to dissolve the soluble separator, thereby separating the sensor module 113 from the sensor module forming substrate. In the present experimental example, acetone, which can dissolve poly(methyl methacrylate), is used as the separator removal solvent. Thereafter, a sensor module 113 is transferred to the therapeutic stimulus generation member 111 so as to be positioned on the top surface of the sensor support plate 112.

f) Thereafter, the electronic thread 11 is cut to fit the preset width and then separated from the electronic thread forming substrate.

Figure 7:
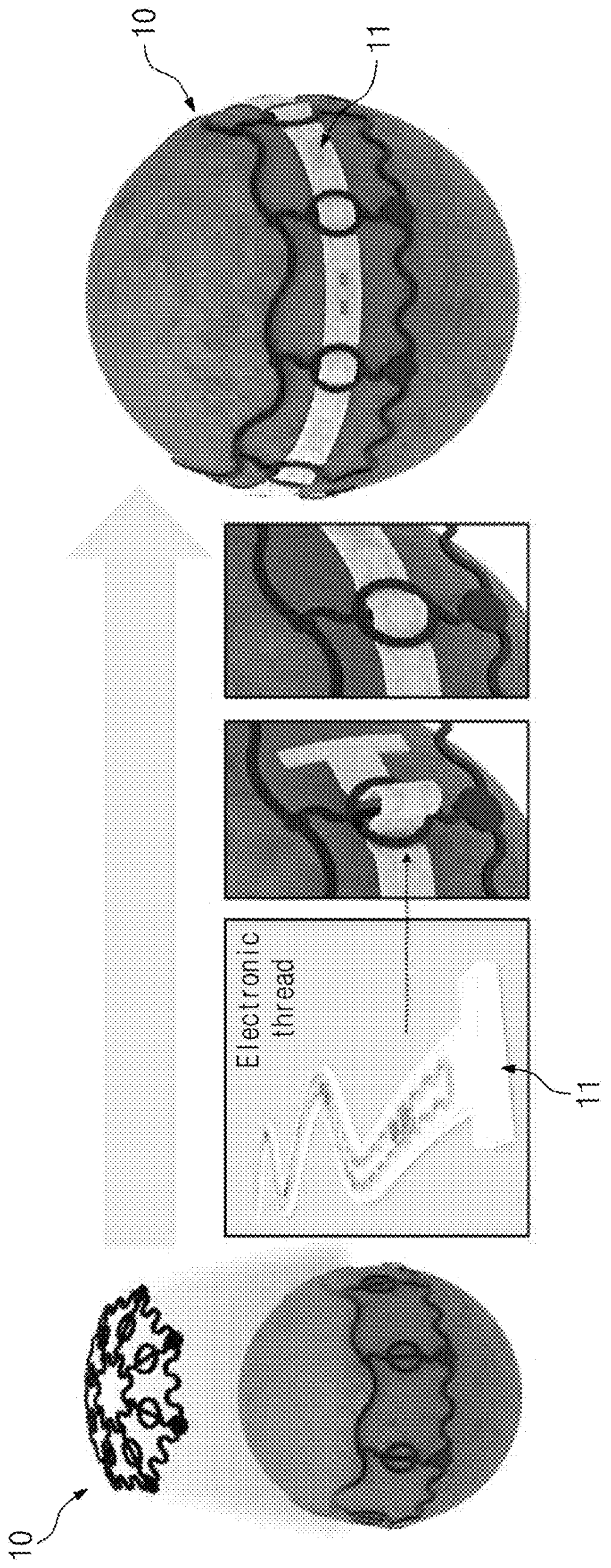
FIG. 7 is a view explaining a state in which the bio-implantable bladder treatment device according to the first embodiment of the present invention is installed in the bladder.

FIG. 7 is a view explaining a state in which the bio-implantable bladder treatment device according to the first embodiment of the present invention is installed in the bladder.

Referring to FIG. 7, in the bio-implantable bladder treatment device 1 according to the first embodiment of the present invention, first, the electronic web 10 is fixed to the outer surface of the bladder while being covered, and accordingly, the electronic web 10 is fixed without an additional surgical procedure or an adhesive material. Thereafter, the electronic thread 11 is inserted into the buckle portion 103 positioned on the electronic web 10 so as to be coupled to the electronic web 10. The number of buckle portions 103 provided in the electronic web 10 may be adjusted depending on the individual or size of the bladder. The electronic thread 11 is inserted such that the sensor module 113 faces the bladder. In the bio-implantable bladder treatment device 1 according to the first embodiment of the present invention, the electronic thread 11 is coupled to the electronic web 10 by the buckle portion 103 of the electronic web 10, and the electronic web is tightly coupled to the electronic thread 11, so that the electronic thread 11 remains a state in close contact with the bladder.

FIG. 8 is a view showing a control relationship of the bio-implantable bladder treatment device according to the first embodiment of the present invention.

Referring to FIG. 8, the controller 13 controls the therapeutic stimulus generation member 111 according to signals received from the sensor. The controller 13 may be installed to be positioned inside a living body (for example, inserted into or attached to skin tissue) or may be positioned outside the living body.

The controller 13 includes an operation control unit 131, a communication unit 132, and a power unit 133.

The operation control unit 131 is provided to be connected to the sensor and the therapeutic stimulus generation member 111. The operation control unit 131 is provided to be connected to each of the LED lead wire 111*a*, the strain sensor lead wire, the temperature sensor lead wire, and the electromyography sensor lead wire. The operation control unit 131 may detect an inflation state of the bladder through signals received from the strain sensor. The operation control unit 131 may detect temperature of the bladder through signals received from the temperature sensor. The operation control unit 131 may detect action potentials occurring in muscles and nerves of the bladder through signals received from the electromyography sensor. When at least one or two of an inflation degree of the bladder, a temperature of the bladder, and an action potential size are greater than equal to a preset value, the operation control unit 131 may operate the therapeutic stimulus generation member 111, so that stimulus for treatment is applied to the bladder. For example, the operation control unit 131 may be configured as a closed-loop system operated in a manner that action potential sizes are repeatedly received when the inflation degree of the bladder and the temperature of the bladder are greater than equal to the preset value, and the therapeutic stimulus generation member 111 is operated when the action potential size is greater than equal to the preset value.

The communication unit 132 transmits signals received by the operation control unit 131 from the sensor, and a control state of the therapeutic stimulus generation member 111 by the operation control unit 131 to an external device. In addition, the communication unit 132 may transmit signals received from the external device to the operation control unit 131, and the operation control unit 131 may control the operating state of the therapeutic stimulus generation member 111 according to the signals transmitted from the communication unit 132. The external device may be a smartphone, a smart pad, a computer, and the like. The communication unit 132 may transmit and receive data with the external device based on a wireless network such as Bluetooth Low Energy.

The power unit 133 stores power for operating the operation control unit 131 and the communication unit 132. The power unit 133 may be configured to include a structure such as an RF coil, so as to be wirelessly charged.

Figure 9:
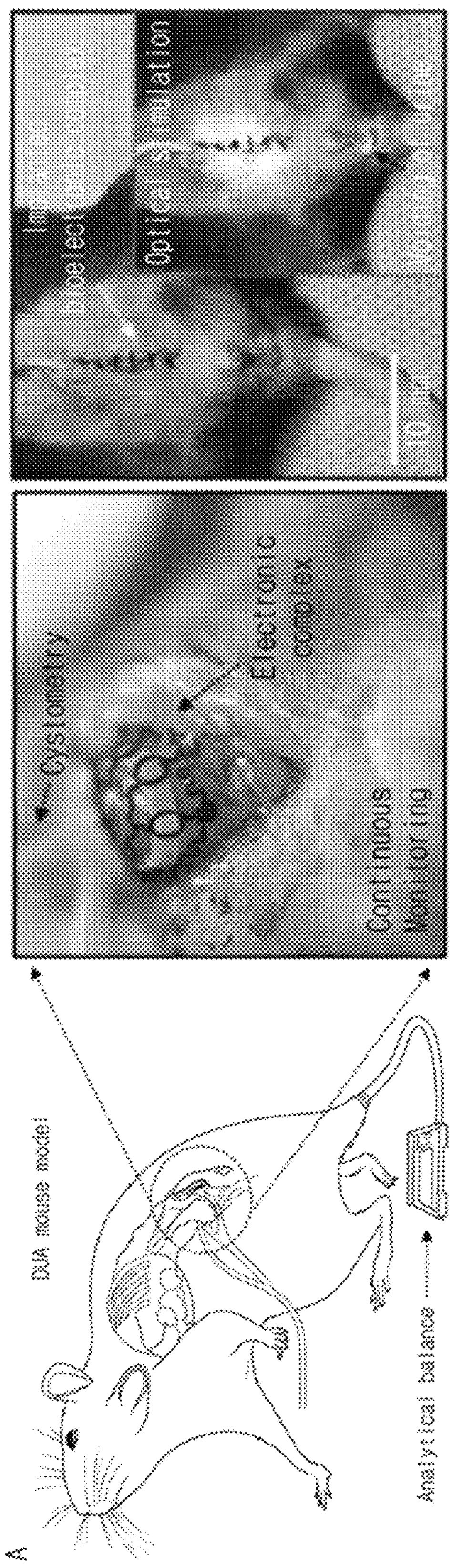
FIG. 9 is a view showing a state in which the bio-implantable bladder treatment device according to the first embodiment of the present invention is used after being attached to the bladder of an actual mouse.
Figure 10:
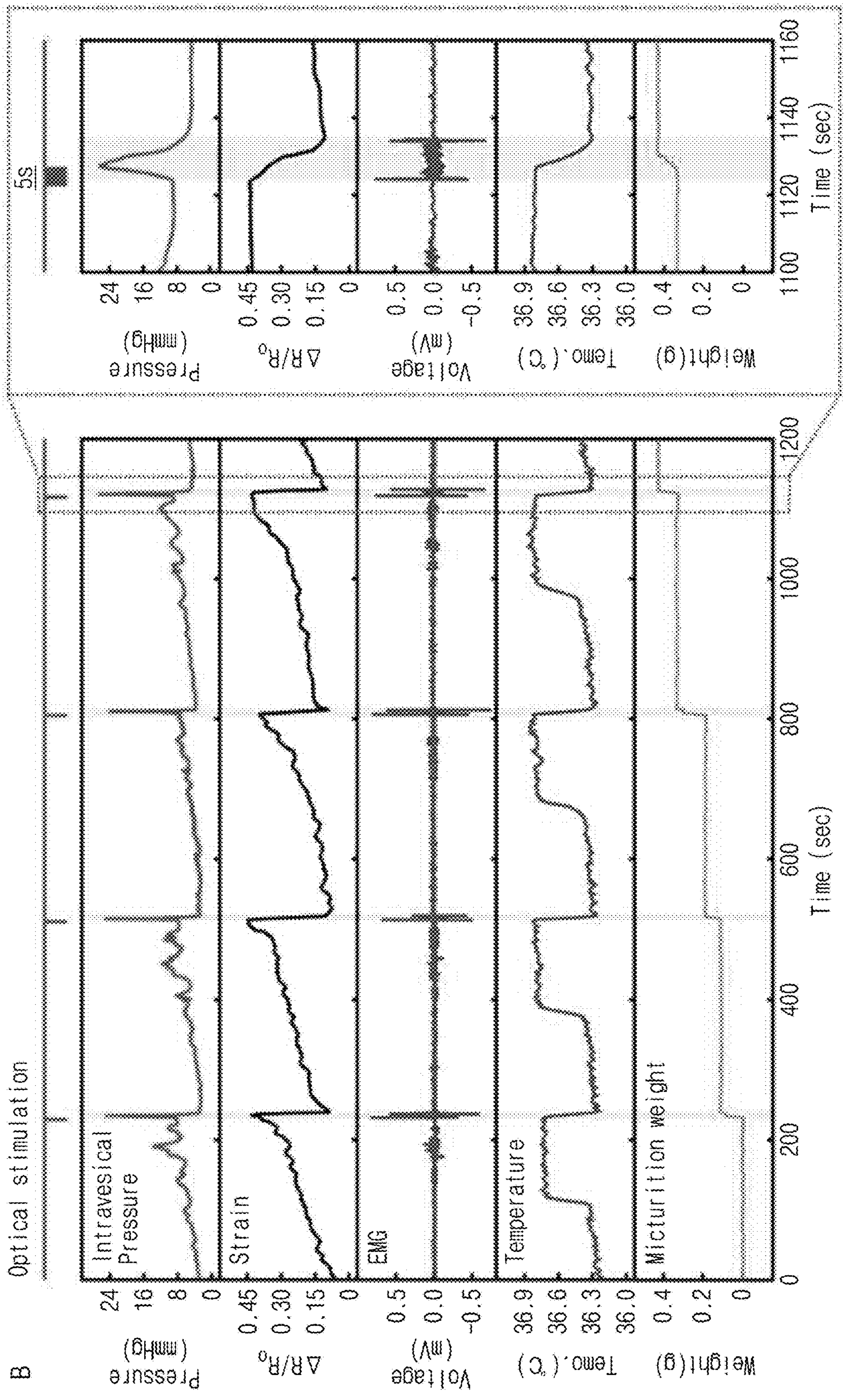
FIG. 10 is a view showing signals generated during the use process according to FIG. 9.

FIG. 9 is a view showing a state in which the bio-implantable bladder treatment device according to the first embodiment of the present invention is used after being attached to the bladder of an actual mouse. FIG. 10 is a view showing signals generated during the use process according to FIG. 9.

Referring to FIGS. 9 and 10, it can be seen that the controller 13 may operate the therapeutic stimulus generation member 111 when the signal received from the sensor is greater than equal to the preset value, and accordingly, urination occurs in response to optogenetic stimulus, and thus the size of the signal received from the sensor is stabilized at a rapid rate. In addition, it can be confirmed that changes in the signal received from the sensor and the operations of the therapeutic stimulus generation member 111 are stably repeated. In addition, the electronic web 10 and the electronic thread 11 may be expanded and contracted, so that the state in close contact with the bladder is maintained even when the bladder is changed in volume.

Figure 11:
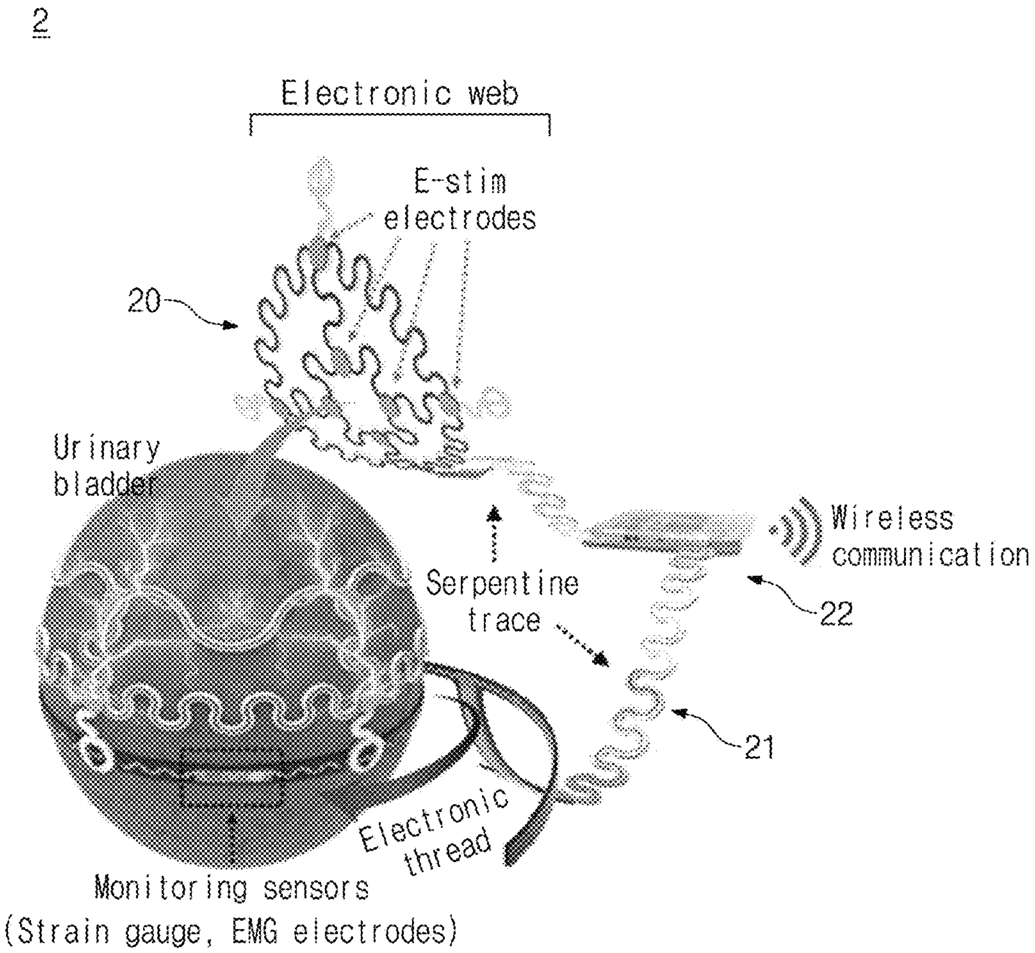
FIG. 11 is a view showing a bio-implantable bladder treatment device according to a second embodiment.
Figure 12:
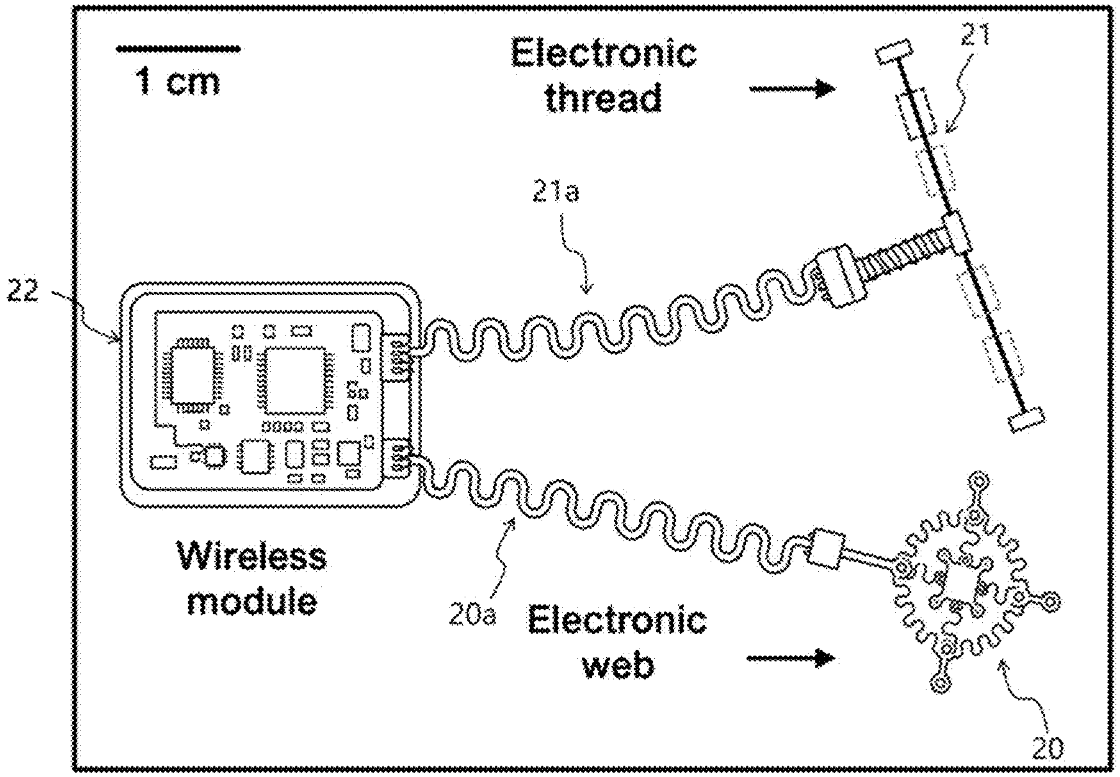
FIG. 12 is an actual photograph of the bio-implantable bladder treatment device according to the second embodiment.

FIG. 11 is a view showing a bio-implantable bladder treatment device according to the second embodiment. FIG. 12 is an actual photograph of the bio-implantable bladder treatment device according to the second embodiment.

Referring to FIGS. 11 and 12, the bio-implantable bladder treatment device 2 according to a second embodiment of the present invention includes an electronic web 20, an electronic thread 21 and a controller 22.

The bio-implantable bladder treatment device 2 according to a second embodiment of the present invention is provided to be installed to an outer circumference of a bladder so as to monitor an activity of the bladder and apply therapeutic stimulus for healing urinary disorders and stimulating a urinary activity to the bladder.

The electronic web 20 is provided to be installable to cover the outer circumference of the bladder. The electronic web 20 may be formed of a polymer material. The electronic web 20 may be formed of a rubber material to have elasticity. For example, the electronic web 20 may be formed of a silicone-based rubber material, biodegradable plastic, biopolymer, poly-butylene adipate terephthalate (PBAT) or the like.

Figure 13:
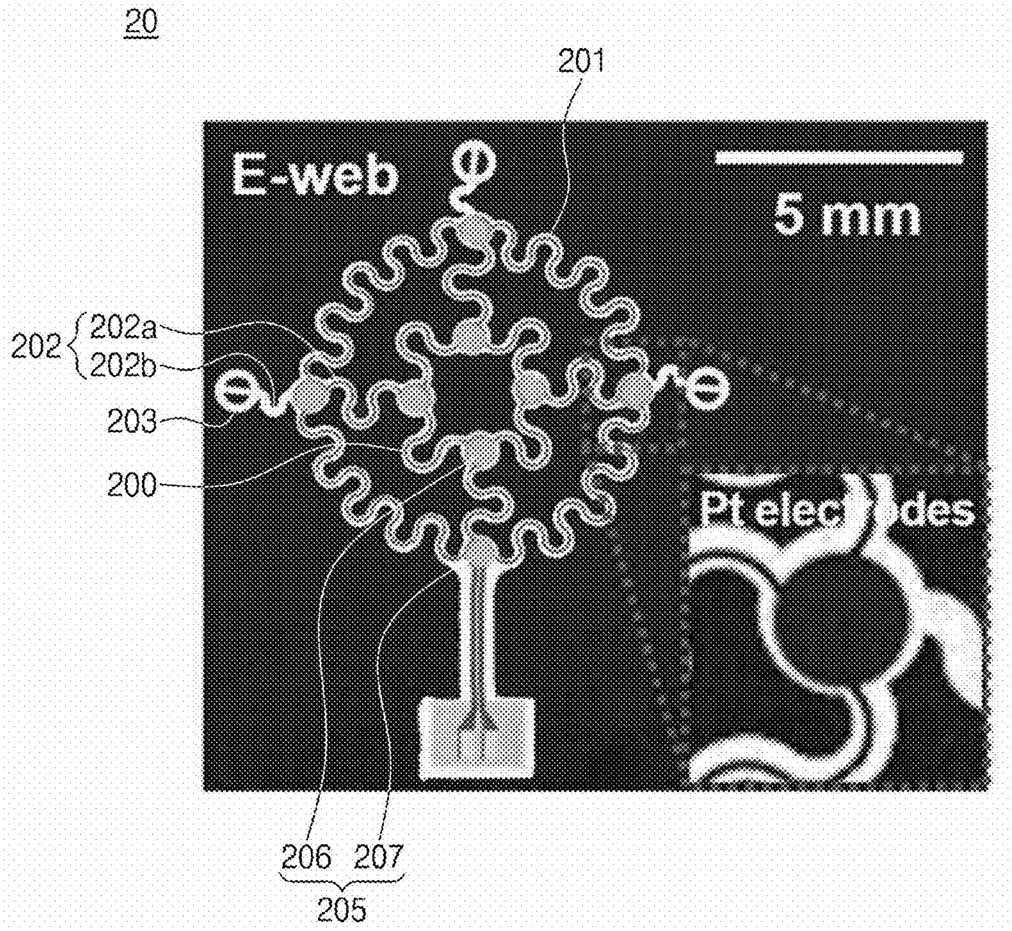
FIG. 13 is a view showing an electronic web in FIG. 11.

FIG. 13 is a view showing an electronic web in FIG. 11.

Referring to FIG. 13, the electronic web 20 includes an inner support portion 200, an outer support portion 201, an auxiliary support portion 202 and a buckle portion 203.

The inner support portion 200 is provided in a ring shape. The inner support portion may be provided to include a winding part in at least one section. Accordingly, the inner support portion 200 may have a shape transformed so that the winding part is straightened.

The outer support portion 201 is provided in a ring shape, and positioned in an area outside the inner support portion 200. The outer support portion 201 may be provided to include a winding part in at least one section. Accordingly, the outer support portion 201 may have a shape transformed so that the winding part is straightened.

The auxiliary support portion 202 is provided to connect the inner support portion 200 and the outer support portion 201 to each other. At least one auxiliary support portion 202 may be provided in a circumferential direction of the inner support portion 200 and the outer support portion 201. The auxiliary support portions 202 may be arranged at equal intervals from each other in the circumferential direction of the inner support portion 200 and the outer support portion 201. In addition, the auxiliary support portions 202 may be arranged to face each other about the inner support portion 200. The auxiliary support portion 202 may be provided to include a winding part in at least one section. Accordingly, the auxiliary support portion 202 may have a shape transformed so that the winding part is straightened.

The auxiliary support portion 202 includes an inner auxiliary support portion 202*a* and an outer auxiliary support portion 202*b*. The inner auxiliary support portion 202*a* has both ends connected to the inner support portion 200 and the outer support portion 201, respectively. The outer auxiliary support portion 202*b* is provided to extend from the outer auxiliary support portion 202*b* in the opposite direction to the inner auxiliary support portion 202*a*.

The buckle portion 203 is provided to be connected to the auxiliary support portion 202. The buckle portion 203 may be connected to the inner auxiliary support portion 202*a* and the outer auxiliary support portion 202*b* FIG. 13 illustrate a case in which the buckle portion 203 is connected to the outer auxiliary support portion 202*b*.

The buckle portion 203 may be provided to form at least one hole, so that a linear structure is inserted and connected thereto. For example, the buckle portion 203 may be formed in a ring shape and connected to a partial section of the auxiliary support portion 202, so that one hole is formed in each of both sides of the auxiliary support portion 202. The buckle portion 203 may be provided on all of the auxiliary support portions 202 or formed on some of the auxiliary support portions 202.

The electronic web 20 may be manufactured in the same method as the electronic web 10 of the bio-implantable bladder treatment device 1 according to the first embodiment of the present invention.

A therapeutic stimulus generation member 205 is positioned on one side of the electronic web 20. The therapeutic stimulus generation member 205 applies to electrical stimulus to the bladder. The therapeutic stimulus generation member 205 includes a first electrode 206 and a second electrode 207. The first electrode 206 and the second electrode 207 are provided to be paired in equal numbers, so that one of the first electrode 206 and the second electrode 207 functions as a source electrode and the other functions as a ground electrode. An electrode connection lead wire for connecting the first electrode 206 to the second electrode 207 may be positioned in the inner auxiliary support portion 202*a*. The therapeutic stimulus generation member 205 may be connected to the controller 22 through a generation member connection lead wire 20*a*. The generation member connection lead wire 20*a* may be provided to include a winding part in at least one section.

The first electrode 206 may be positioned in the inner support portion 200, and the second electrode 207 may be positioned in the outer support portion 201. A plurality of first electrodes 206 and second electrodes 207 may be provided along the circumferential direction of the inner support portion 200 and the outer support portion 201, respectively. The first electrode 206 and the second electrode 207 may be positioned in areas in which the inner auxiliary support portions 202*a* are connected to the inner support portion 200 and the outer support portion 201, respectively. A plurality of first electrodes 206 and second electrodes 207 may be positioned at equal intervals along the circumferential direction of the inner support portion 200 and the outer support portion 201, respectively.

The therapeutic stimulus generation member 205 is formed by attaching a metallic material, such as platinum (Pt) or iridium (Ir), to one surface of the electronic web 20. For example, the therapeutic stimulus generation member 205 may be formed on the electronic web 20 through an electroplating scheme.

Figure 14:
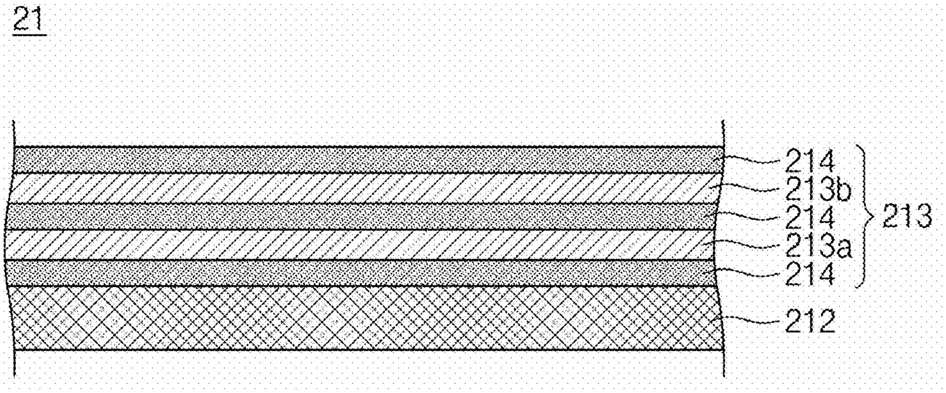
FIG. 14 is a view schematically showing a longitudinal sectional structure of an electronic thread in FIG. 11.

FIG. 14 is a view schematically showing a longitudinal sectional structure of an electronic thread in FIG. 11.

Referring to FIG. 14, the electronic thread 21 includes a sensor support plate 212 and a sensor module 213.

The electronic thread 21 measures a state of the bladder.

The sensor support plate 212 is provided as a thread structure having a preset width. The width of the sensor support plate 212 is provided to correspond to a size of the hole of the buckle portion 203 so as to be inserted into the buckle portion 203. The sensor support plate 212 is formed of a polymer material. For example, the sensor support plate 212 may be formed of a silicone-based rubber material, biodegradable plastic, biopolymer, poly-butylene adipate terephthalate (PBAT) or the like. The sensor support plate 212 may have a thickness of tens of micrometers.

The sensor module 213 detects a state of the bladder. The sensor module 213 is attached to a top surface of the sensor support plate 212. The sensor module 213 includes a sensor layer 213*a* and 213*b* and a sensor protective layer 214. The sensor module 213 may be connected to the controller 22 through a sensor module connection lead wire 21*a*. The sensor module connection lead wire 21*a* may be provided to include a winding part in at least one section.

The sensor layer 213*a* and 213*b* is provided to include a sensor that detects a state of the bladder. The sensor layer 213*a* and 213*b* includes a strain sensor layer 213*a* and an electromyography sensor layer 213*b*. The sensor includes a strain sensor and an electromyography sensor.

The strain sensor layer 213*a* is provided to detect strain. The strain sensor layer 213*a* includes a strain sensor and a strain sensor lead wire for connecting the strain sensor.

The electromyography sensor layer 213*b* is provided to detect electromyography. The electromyography sensor layer 213*b* includes an electromyography sensor and an electromyography sensor lead wire for connecting the electromyography sensor.

The strain sensor layer 213*a* and the electromyography sensor layer 213*b* are laminated with each other. The strain sensor layer 213*a* and the electromyography sensor layer 213*b* have no limit for the laminated sequence. In other words, the strain sensor layer 213*a* may be positioned below, or the electromyography sensor layer 213*b* may be positioned below.

The sensor protective layer 214 is positioned between the strain sensor layer 213*a* and the electromyography sensor layer 213*b*. In addition, the sensor protective layer 214 may be positioned on top and bottom surfaces of the sensor layers 213*a* and 213*b* in which the strain sensor layer 213*a* and the electromyography sensor layer 213*b* are laminated.

Since the method for manufacturing of the electronic thread 21 is the same as or similar to FIG. 6 except that the sensor support plate 212 is replaced with the support plate 110 in the method for manufacturing the electronic thread 11 according to the first embodiment and the manufacturing process of the stimulus generation member of the electronic thread 11 according to the first embodiment is omitted, duplicate descriptions will be omitted.

Figure 15:
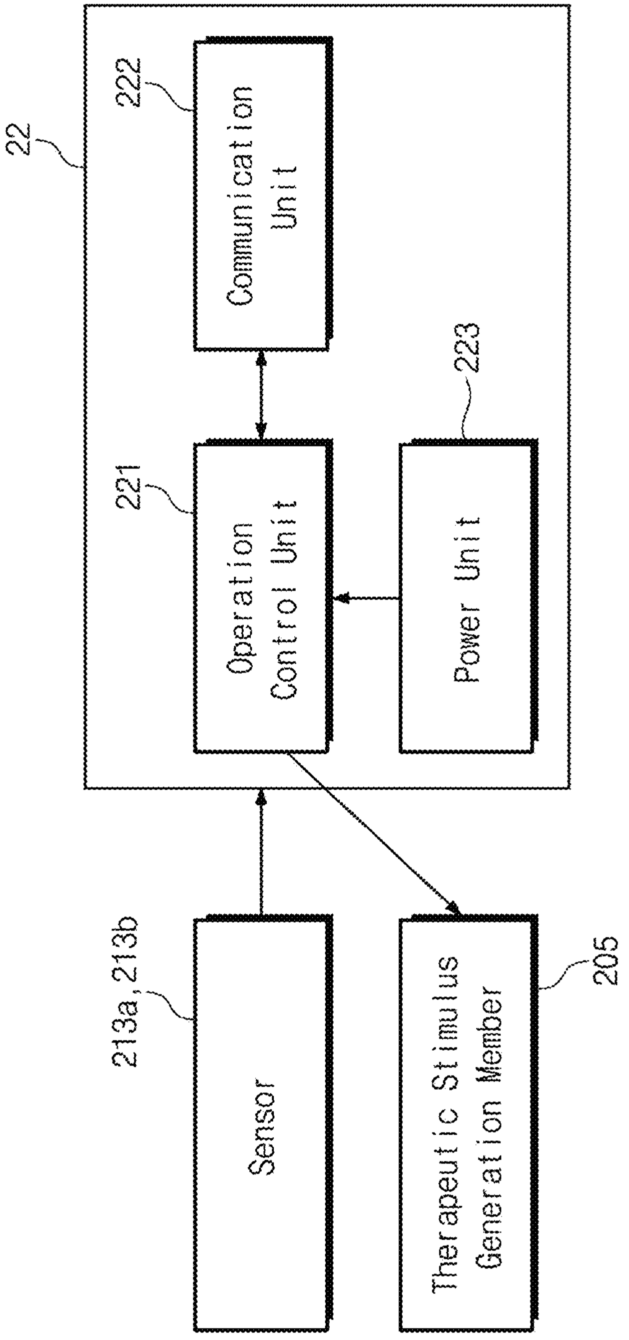
FIG. 15 is a view showing a control relationship of the bio-implantable bladder treatment device according to the second embodiment of the present invention.

FIG. 15 is a view showing a control relationship of the bio-implantable bladder treatment device according to a second embodiment of the present invention.

Referring to FIG. 15, the controller 22 controls the therapeutic stimulus generation member 205 according to signals received from the sensor. The controller 22 may be installed to be positioned inside a living body (for example, inserted into or attached to skin tissue) or may be positioned outside the living body.

The controller 22 includes an operation control unit 221, a communication unit 222, and a power unit 223.

The operation control unit 221 is provided to be connected to the sensor and the therapeutic stimulus generation member 205. The operation control unit 221 may be connected to the therapeutic stimulus generation member 205 through the generation member connection lead wire 20*a*. The operation control unit 221 is connected to each of the strain sensor lead wire and the electromyography sensor lead wire through the sensor module connection lead wire 21*a*. The operation control unit 221 may detect an inflation state of the bladder through signals received from the strain sensor. The operation control unit 221 may detect action potentials occurring in muscles and nerves of the bladder through signals received from the electromyography sensor. When at least one or two of an inflation degree of the bladder and an action potential size are greater than equal to a preset value, the operation control unit 221 may operate the therapeutic stimulus generation member 205, so that stimulus for treatment is applied to the bladder. For example, the operation control unit 221 may be configured as a closed-loop system operated in a manner that the therapeutic stimulus generation member 205 is operated when at least one of the inflation degree of the bladder and the action potential size are greater than equal to a preset value.

The communication unit 222 transmits signals received by the operation control unit 221 from the sensor, and a control state of the therapeutic stimulus generation member 205 by the operation control unit 221 to an external device. In addition, the communication unit 222 may transmit signals received from the external device to the operation control unit 221, and The operation control unit 221 may control the operating state of the therapeutic stimulus generation member 205 according to the signals transmitted from the communication unit 222. The external device may be a smartphone, a smart pad, a computer, and the like. The communication unit 222 may transmit and receive data with the external device based on a wireless network such as Bluetooth Low Energy.

The power unit 223 stores power for operating the operation control unit 221 and the communication unit 222. The power unit 223 may be configured to include a structure such as an RF coil, so as to be wirelessly charged.

Figure 16:
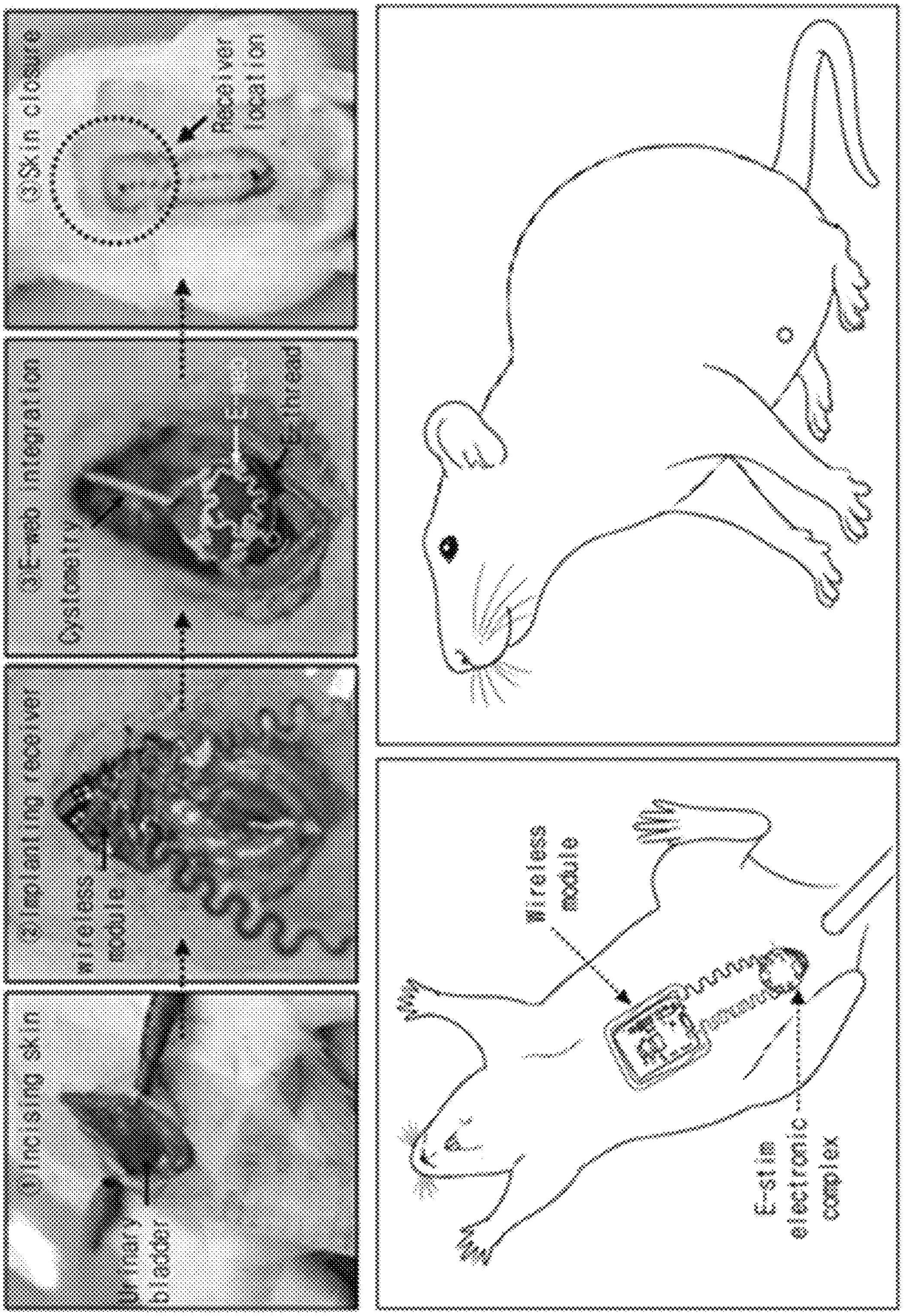
FIG. 16 is a view showing a state in which the bio-implantable bladder treatment device according to the second embodiment of the present invention is used after being attached to the bladder of an actual mouse.
Figure 17:
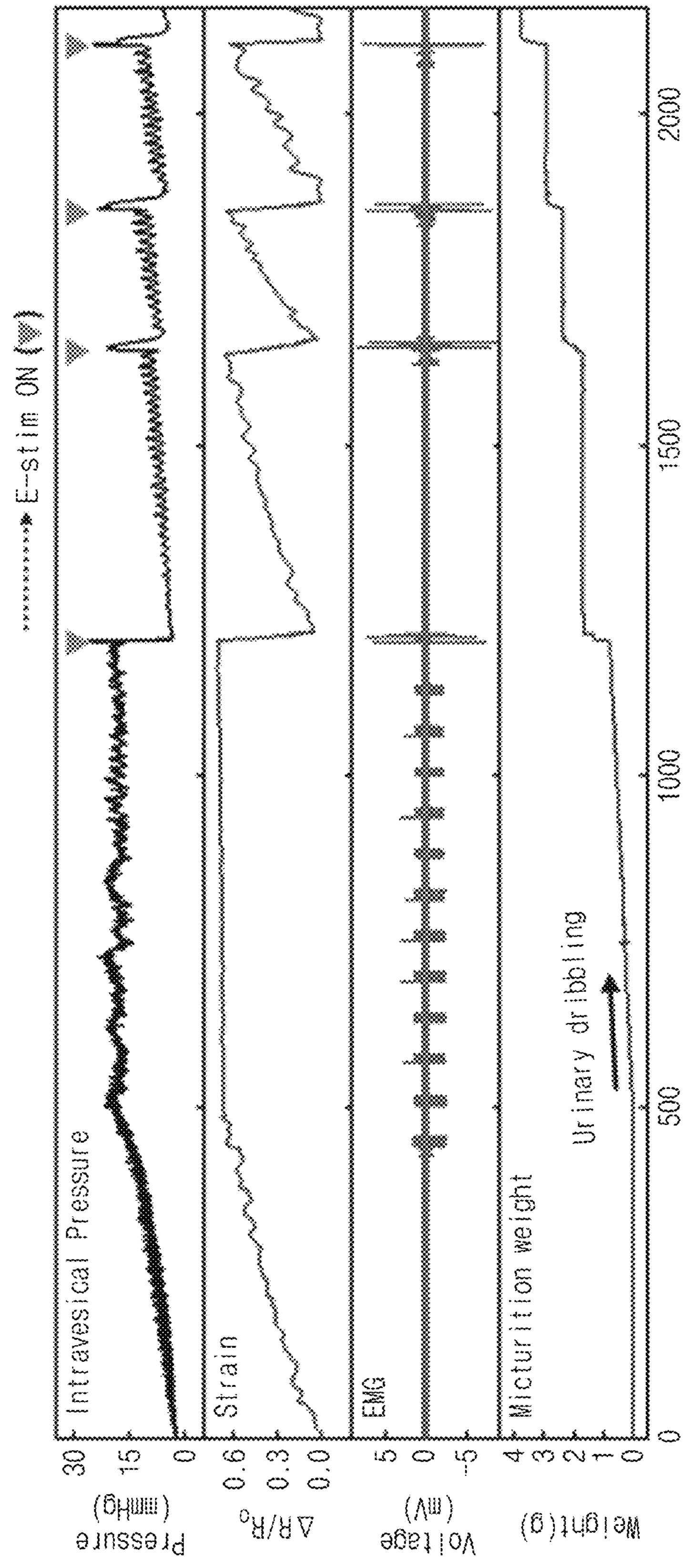
FIG. 17 is a view showing signals generated during the use process according to FIG. 16.

FIG. 16 is a view showing a state in which the bio-implantable bladder treatment device according to the second embodiment of the present invention is used after being attached to the bladder of an actual mouse. FIG. 17 is a view showing signals generated during the use process according to FIG. 16.

Referring to FIGS. 16 and 17, it can be seen that the controller 22 may operate the therapeutic stimulus generation member 205 when the signal received from the sensor is greater than equal to the preset value, and accordingly, urination occurs in response to electrical stimulus, and thus the size of the signal received from the sensor is stabilized at a rapid rate. In addition, it can be confirmed that changes in the signal received from the sensor and the operations of the therapeutic stimulus generation member 205 are stably repeated. In addition, the electronic web 20 and the electronic thread 21 may be expanded and contracted, so that the state in close contact with the bladder is maintained even when the bladder is changed in volume.

Although the present invention has been described in detail with reference to the exemplary embodiments, the present invention is not limited to the specific embodiments and shall be interpreted by the following claims. In addition, it will be apparent that a person having ordinary skill in the art may carry out various deformations and modifications for the embodiments described as above within the scope without departing from the present invention.

The invention claimed is:

1. A bio-implantable bladder treatment device comprising:

an electronic web installable to cover an outer circumference of a bladder; and an electronic thread inserted into the electronic web so as to be coupled to the electronic web to measure a state of the bladder, wherein the thread includes, a support plate made of an elastic material provided as a thread structure having a predetermined width;

a therapeutic stimulus generating member attached to an upper surface of the support plate and generating stimulation;

a sensor support plate attached to an upper surface of the therapeutic stimulus generating member and provided from an elastic material;

a plurality of detection sensors attached to an upper surface of the sensor support plate and arranged in a stacked manner to measure a state of the bladder; and a sensor protection layer provided between each of the detection sensors.

2. The bio-implantable bladder treatment device of claim 1, wherein the electronic web includes:

an inner support portion provided in a ring shape;

an outer support portion provided in a ring shape and positioned in an area outside the inner support portion; and an auxiliary support portion for connecting the inner support portion and the outer support portion to each other.

3. The bio-implantable bladder treatment device of claim 2, wherein the electronic web further includes:

a buckle portion connected to the auxiliary support portion and formed therein with a hole into which the electronic thread is inserted.

4. The bio-implantable bladder treatment device of claim 1, wherein the electronic web is formed of an elastic material.

5. The bio-implantable bladder treatment device of claim 1, further comprising:

a therapeutic stimulus generation member positioned on one side of the electronic web to generate electrical stimulus.

6. The bio-implantable bladder treatment device of claim 5, wherein the therapeutic stimulus generation member includes a first electrode and a second electrode paired with each other.

7. The bio-implantable bladder treatment device of claim 1, wherein the sensor includes a strain sensor, a temperature sensor and an electromyography sensor, wherein the sensor protection layer is provided between the strain sensor and the temperature sensor, and between the temperature sensor and the electromyography sensor, respectively.

8. The bio-implantable bladder treatment device of claim 1, further comprising:

a controller connected to the sensor to monitor an activity of the bladder through received signals.

* * * * *